(12) United States Patent
Wang et al.

(10) Patent No.: US 10,378,019 B2
(45) Date of Patent: Aug. 13, 2019

(54) PREMETHYLATION OF DNA FOR HIGH EFFICIENCY TRANSFORMATION OF CYANOBACTERIA

(71) Applicants: Bo Wang, Tempe, AZ (US); Weiwen Zhang, Tianjin (CN); Deirdre Meldrum, Phoenix, AZ (US)

(72) Inventors: Bo Wang, Tempe, AZ (US); Weiwen Zhang, Tianjin (CN); Deirdre Meldrum, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 14/842,671

(22) Filed: Sep. 1, 2015

(65) Prior Publication Data
US 2016/0060643 A1     Mar. 3, 2016

Related U.S. Application Data

(60) Provisional application No. 62/045,314, filed on Sep. 3, 2014.

(51) Int. Cl.
*C12N 15/74* (2006.01)

(52) U.S. Cl.
CPC .................................. *C12N 15/74* (2013.01)

(58) Field of Classification Search
CPC ........ A01H 17/00; C12N 15/63; C12N 15/64; C12N 15/67; C12N 15/70; C12N 15/74; C12N 15/8201; C12N 15/87; C12N 15/102; C12N 2310/3521

See application file for complete search history.

(56) References Cited

PUBLICATIONS

Scharnagl et al., (J. of Bacteriol. 1998. vol. 180(16):4116-4122).*
Wang et al., (Metab Eng. 2013. Mar. 2013. vol. 16:68-77. Epub Jan. 16, 2013).*
Elhai et al., (J. of Bacteriology. Mar. 1997. vol. 179.No. 6: 1998-2005).*
Kufryk et al., FEMS. Micro. Letters. Jan. 2002. vol. 206. Issue (2): pp. 215-219).*
Wang B et al. 2015. Premethylation of foreign DNA Improves Integrative Transformation Efficiency in *Synechocystis* sp. Strain PCC 6803. Appl. and Environ. Microbiology. 81. 8500-8506.
Ungerer J et al. 2012. Sustained photosynthetic conversion of CO2 to ethylene in recombinant cyanobacterium Synechocystis 6803. Energy Environ.Sci. 5. 8998-9006.

* cited by examiner

*Primary Examiner* — Jana A Hines
(74) *Attorney, Agent, or Firm* — Gavin J. Milczarek-Desai; Quarles & Brady LLP

(57) ABSTRACT

Methods of pre-methylation of foreign DNA to improve genetic transformation in cyanobacterium. Two Type II methyltransferase-encoding genes, i.e., M (sll0729) and C (slr0214), were cloned from the chromosome of *Synechocystis* sp. PCC 6803 (hereafter *Synechocystis* 6803) and expressed in *E. coli* that harbors the integrative plasmid pBS-SPtK or pJU105. After pre-methylation in *E. coli*, the integrative plasmids were extracted and used for transformation of *Synechocystis* 6803. The results showed that expression of slr0214 in the integrative-plasmid-harboring *E. coli* cells before DNA preparation resulted in orders of magnitude higher efficiency in the following integrative transformation of *Synechocystis* 6803.

20 Claims, 6 Drawing Sheets

Specification includes a Sequence Listing.

PREMETHYLATION OF DNA FOR HIGH EFFICIENCY TRANSFORMATION OF CYANOBACTERIA

CROSS-REFERENCE TO RELATED APPLICATIONS

This application claims priority to U.S. Provisional Patent Application No. 62/045,314, filed Sep. 3, 2014, the entire contents of which is incorporated herein in its entirety by reference.

TECHNICAL FIELD

This disclosure relates in general to methods of transforming cells and more specifically to methods of high efficiency transformation of cyanobacteria.

BACKGROUND

Driven by energy sustainability and environmental concerns, increasing endeavors have been made in developing and applying synthetic biology tools in cyanobacteria in recent years. One of the key elements to assure success of such efforts is to establish genetic transformation methodologies of high efficiency in cyanobacteria. Since its first demonstration in cyanobacterium *Anacystis nidulans* 602 in 1970, genetic transformation protocols for a variety of cyanobacterial species have been developed and optimized. However, despite the exciting achievement made in the past decades, the transformation efficiency in cyanobacteria is still typically lower than other model systems, such as *E. coli* and yeast.

SUMMARY

Embodiments disclosed herein relate to methods of pretreating exogenous DNA via expressing methyltransferase such that the DNA is less prone to cleavage by restriction endonucleases. For example, expressing methyltransferase of *Synechocystis* sp. PCC 6803 in recombinant *E. coli* is able to increase the *Synechocystis* transformation efficiency by 161-fold.

Further, the methods described herein are independent of other optimization strategies, and can be combined with other optimization strategies to further increase the efficiency.

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

DESCRIPTION OF DRAWINGS

FIG. 1 Integrative plasmid pBS-SPtK and schematic representation of the homologous recombination. Arm 1, the left homologous DNA fragment, part of which is slr1362. Arm 2, the right homologous DNA fragment, part of which is sll1274. Asterisks indicate the sites with DNA sequence 5'-GGCC-3'; black arrow heads represent the sites with DNA sequence 5'-GCGATCGC-3' (PvuI site underlined).

FIG. 2 Help Plasmids used to express DNA methylases of *Synechocystis* 6803 in *E. coli*. (A) Scheme of the Help Plasmids. Gene(s) X represents *Synechocystis* methylase genes. (B) Genetic structures of the region of Gene(s) X on Help Plasmids. M, sll0729; C, slr0214.

DETAILED DESCRIPTION

Figure 3:
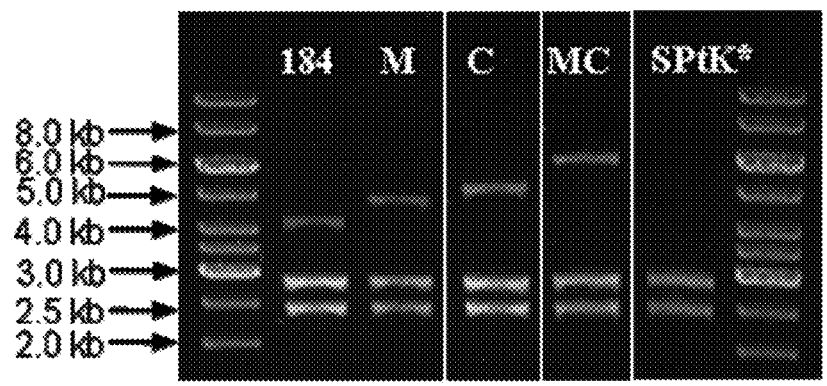
FIG. 3 Confirmation of the coexistence of integrative plasmid pBS-SPtK and each Help Plasmid. The leftmost and rightmost lanes are standard DNA ladders. Lanes 184, M, C, MC indicate coexistence of the integrative plasmid pBS-SPtK with pACYC184 (Control 1), pAC-M, pAC-C or pAC-MC, respectively. Lane SPtK*, existence of pBS-SPtK only (Control 2).

Cyanobacteria are the model species in studying photosynthesis and in recent years are gaining increasing attention in microbial production of renewable fuels and chemicals due to their capability in harvesting solar energy and recycling carbon dioxide.

However, transformation efficiency in cyanobacteria is generally much lower compared to model microbial species, such as *E. coli* and yeast, setting a significant barrier to harnessing this type of microorganisms.

To establish a high-efficiency transformation protocol in cyanobacteria, we investigated the effects of pre-methylation of foreign DNA on the genetic transformation in a model cyanobacterium, *Synechocystis* sp. PCC 6803. In this innovative protocol, the transformation efficiency in *Synechocystis* sp. PCC 6803 is increased by more than two orders of magnitude.

Most bacteria carry specific restriction-modification (RM) systems that are able to recognize and degrade foreign DNA from the self DNA. Each RM system typically consists of one methylase (also called methyltransferase) and one restriction endonuclease; the methylase protects the self DNA from restriction digestion by methylating the nucleotides at specific DNA sequences (i.e., restriction sites), while the foreign DNA which usually bears a different methylation pattern would be recognized and degraded by the endonucleases.

Cyanobacterium *Synechocystis* sp. PCC 6803 (hereafter *Synechocystis* 6803) is naturally transformable and the transformation procedure has been optimized since decades ago. In this embodiment, two cytosine-specific methylase genes, sll0729 and slr0214, have been cloned from the chromosome of *Synechocystis* 6803. Specifically, gene slr0214 from *Synechocystis* 6803 encodes a cytosine-specific methyltransferase that probably targets the first cytosine of the PvuI site (5'-CGATCG-3'); and gene sll0729 has been predicted to encode a cytosine-specific methyltransferase that recognizes and functions on the cytosine base(s) of the sequence 5'-GGCC-3'. These two genes were cloned and co-expressed by well known methods in the integrative-plasmid-harboring *E. coli*, and the effects of pre-methylation of foreign DNA on the integrative transformation efficiency in *Synechocystis* 6803 was investigated.

Strains and Culture Conditions.

All strains used in this invention are listed in Table 1. *E. coli* strain XL1-Blue MRF' (Stratagene, La Jolla, Calif., USA) was used as the host for all plasmids. All recombinant *E. coli* strains were cultivated in LB medium under 37° C., 175 rpm. Solid LB plates were prepared by adding agar to a final concentration of 1.5% (w/v). Antibiotics were supplemented into the LB medium to final concentrations of 100 µg/ml for ampicillin and 100 µg/ml for chlorhamphenicol when necessary to maintain the plasmids. *Synechocystis* 6803 was cultivated in BG11 medium under light with intensity of 35 µE m$^{-2}$ s$^{-1}$. 10 mM TES (pH 8.2), 3 g/L thiosulfate and 1.5% (w/v) agar was supplemented to BG11 before autoclaving to prepare solid agar plates. A final concentration of 10 µg/ml kanamycin was supplemented into the BG11 plates to select successful transformants.

Construction of Plasmids.

Figures 1, 2:
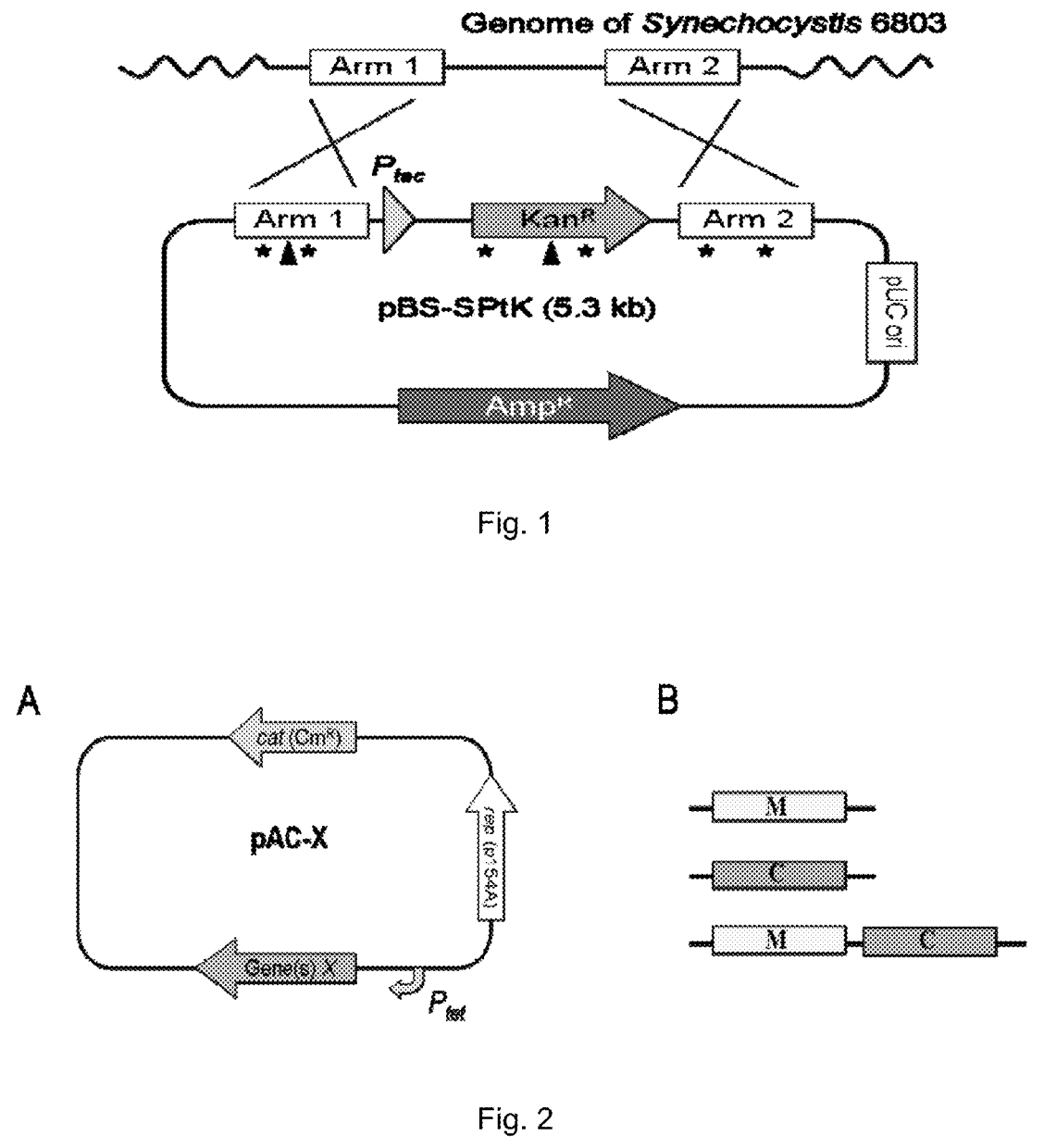

The integrative plasmid pBS-SPtK targeting the *Synechocystis* chromosome was constructed as described previously (36). The schematic structure of plasmid pBS-SPtK is illustrated in FIG. 1. Help Plasmids used to express *Synechocystis* methylases were constructed as follows. Gene sll0729 (M) which encodes a modification methylase was cloned from the genome of *Synechocystis* 6803, digested with BglII and SalI, and inserted between the BamHI and SalI sites on plasmid pACYC184 to construct plasmid pAC-M. Similarly, gene slr0214 (C; encoding a cytosine-specific methyltransferase) was cloned from the genome of *Synechocystis* 6803, digested with BamHI and SalI, and inserted between the BamHI and SalI sites on and inserted into pACYC184 to constructed plasmid pAC-C. Gene C was digested with BamHI and SalI and placed downstream of the gene M on plasmid pAC-M to construct plasmid pAC-MC. When each gene was cloned by PCR, the native RBS was included. Particularly, a point mutation was introduced by the primer in PCR amplification of gene M to result in a stronger RBS (Table 2). To optimize the 5'-untranslated region for gene M, primers Ptet2 and MMS5 were used in PCR with plasmid pAC-M or pAC-MC as the template. The PCR products were digested with EcoRV before being ligated to form plasmid pAC-Mv and pAC-MCv, respectively. To optimize the 5'-untranslated region for gene C, primers CSM3 and CSM4 were used in PCR with plasmid pAC-C as the template. The PCR products were digested with HindIII and BamHI before being inserted between these two sites on plasmid pACYC184 to construct plasmid pAC-Cv. High fidelity *Phusion* DNA polymerase was utilized in all PCR amplifications. All the plasmid constructs were confirmed by DNA sequencing. All plasmids were listed in Table 1, and the PCR primers are listed in Table 2.

Preparation of DNA for *Synechocystis* Transformation.

The integrative plasmid pBS-SPtK, designated to target the genome of *Synechocystis* 6803, is schematically represented in FIG. 1. The kanamycin resistance gene was placed under a strong promoter $P_{tac}$. The two DNA fragments, Arm 1 and Arm 2, designed to target the genome of *Synechocystis* 6803 via homologous recombination were about 650 bp each (FIG. 1).

A total of three Help Plasmids were constructed to express *Synechocystis* DNA methylase(s) in *E. coli* (FIG. 2). Each Help Plasmid has an origin of plasmid pACYC184 which is compatible with the pUC origin of the integrative plasmid pBS-SPtK. Therefore each Help Plasmid could coexist with the integrative plasmid in the *E. coli* host. After co-transformation of *E. coli*, the coexistence of the integratiove plasmid pBS-SPtK and the Help Plasmid was confirmed by restriction digestion followed by agarose gel electrophoresis (FIG. 3). The integrative plasmid was digested to 2.5 kb and 2.8 kb; the Help Plasmids were linearized to DNA fragments bigger than 4.0 kb (FIG. 3).

As the DNA concentration is critical to the transformation efficiency of *Synechocystis*, each plasmid mixture sample was further analyzed by Bioanalyzer to quantify the DNA concentration for the integrative plasmid pBS-SPtK. After three replicates of DNA analysis via Bioanalyzer, each DNA mixture sample was then diluted by dH$_2$O to a final concentration of 100 µg/ml and used for transformation of *Synechocystis* 6803.

Transformation of *Synechocystis*.

*Synechocystis* 6803 was grown until OD$_{730}$=~0.4. Then, 50 µl of the culture was taken into each 1.5 ml Eppendorf tube and mixed with 5.5 µl of above plasmid mixture. The final concentration of the integrative plasmid was 10 µg/ml in each transformation mixture. The Eppendorf tubes were then incubated at 30° C. under light with an intensity of ~15 µE m$^{-2}$ s$^{-1}$ for 5 h, shaken once at 2.5 h. The transformation mixture was transferred onto BG11 plates amended with 10 µg/ml kanamycin. Colonies were counted after 1-2 weeks.

Effect of Pre-Methylation of DNA on the Integrative Transformation Efficiency.

Figure 4:
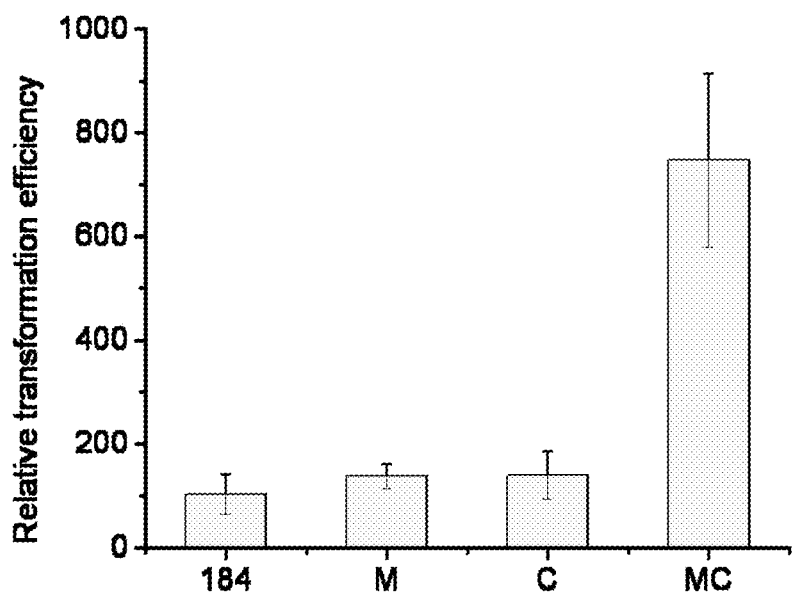
FIG. 4 Transformation efficiency of the integrative plasmid pBS-SPtK into *Synechocystis* 6803. Lanes 184, M, C and MC indicate the effect of coexistence with plasmid pACYC184 (Control 1), pAC-M, pAC-C or pAC-MC on the transformation efficiency of plasmid pBS-SPtK.

Because pBS-SPtK can not replicate and acts as an integrative plasmid when transferred into cyanobacterium *Synechocystis* 6803, *Synechocystis* cells would grow on the kanamycin-amended BG11 plates only when the kanamycin resistance marker has been integrated into the genome via homologous recombination. Hence, the number of the colonies shown on the kanamycin-amended BG11 plates can be used as an indicator of the integrative transformation efficiency. As shown in FIG. 4, expression of individual *Synechocystis* methylase M or C in the pBS-SPtK harboring *E. coli* host has exerted marginal effects on the transformation efficiency in *Synechocystis* 6803 (FIG. 4). However, after the integrative plasmid pBS-SPtK was co-transferred with the Help Plasmid pAC-MC and propagated in *E. coli*, the integrative transformation of *Synechocystis* 6803 by pBS-SPtK dramatically increased, about 7.5-fold higher than the control (FIG. 4). The results suggested that either there was cooperation of M (Sll0729) and C (Slr0214) on methylation of the integrative plasmid pBS-SPtK or the expression of methylase C (Slr0214) was very poor via plasmid pAC-C but was significantly improved when expressed via plasmid pAC-MC. To date, no study was reported on cooperation of two or multiple methylase enzymes (especially those targeting different feature sequences) during DNA methylation.

Improved Expression of Methylase C (Slr0214) Facilitates Integrative transformation.

Expression of methylase genes in the pSPtK-harboring *E. coli* cells was firstly confirmed by analyzing the mRNA using RT-qPCR technique. In our case, expression of methylase genes M and C was driven by the $P_{tet}$ promoter on the pACYC derived plasmids. In order to find out if adding inducer tetracycline would play an impact on the transcription level, we added 10 μg/ml tetracycline into the LB culture medium when the $OD_{600}$ reached ~0.5. Flasks were then wrapped by aluminum foil to avoid any degradation of tetracycline caused by light. We discovered that the mRNA abundance of the target methylase genes in the uninduced *E. coli* cells was at the same level as that of the induced cells, indicating that $P_{tet}$ promoter was efficient enough in expressing the methylase genes M and C without using any tetracycline.

Next, the Gibbs free energy related to the translation initiation rate (TIR) of each methylase genes was calculated using previously established method. The results showed that the $\Delta G_{total}$ was 5.13 kcal/mol for translation initiation of gene M when expressed on pAC-M and pAC-MC, indicating expression of gene M was very poor. The $\Delta G_{total}$ for gene C translation initiation on plasmid pAC-MC was smaller than that of pAC-C which resulted in 3.4-fold higher TIR on pAC-MC compared to that on pAC-C (Table 3). It is consistent with the aforementioned improved integrative transformation efficiency using pAC-MC as the Help Plasmid (FIG. 4).

The 5-untranslated regions of genes M and C were modified by constructing plasmids pAC-Mv, pAC-Cv and pAC-MCv. In the new constructs, the $\Delta G_{total}$ value for genes M and C were much smaller, and the TIRs for genes M and C on plasmids pAC-Mv and pAC-Cv were increased by 25- and 151-fold, respectively, compared to the parent plasmids pAC-M and pAC-C (Table 3). When these redesigned and subsequently constructed Help Plasmids were co-transferred with the integrative plasmid pSPtK into *E. coli* hosts before transforming *Synechocystis* 680, it resulted in up to 161-fold higher efficiency in the later integrative transformation of *Synechocystis* 6803 (FIG. 5).

Figure 5:
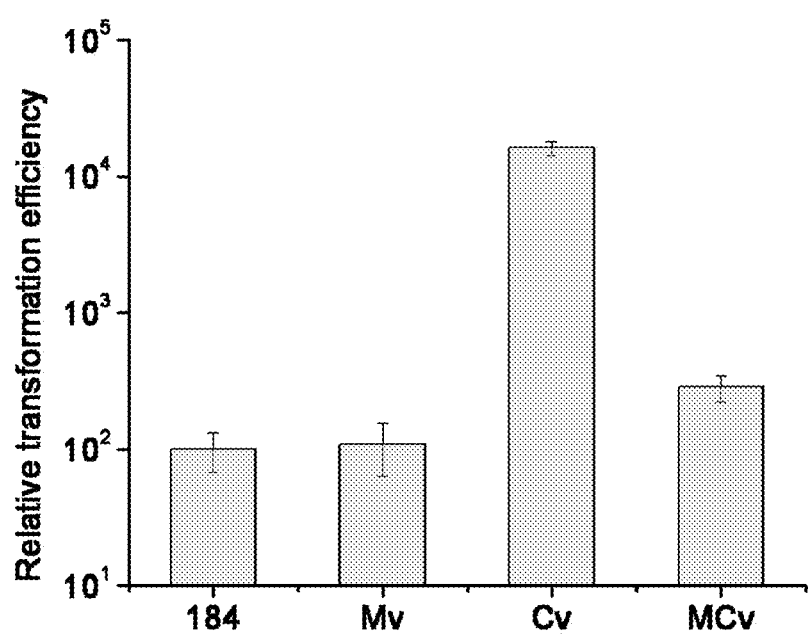
FIG. 5 Transformation efficiency after optimizing the translation of methylase genes.
Figure 6:
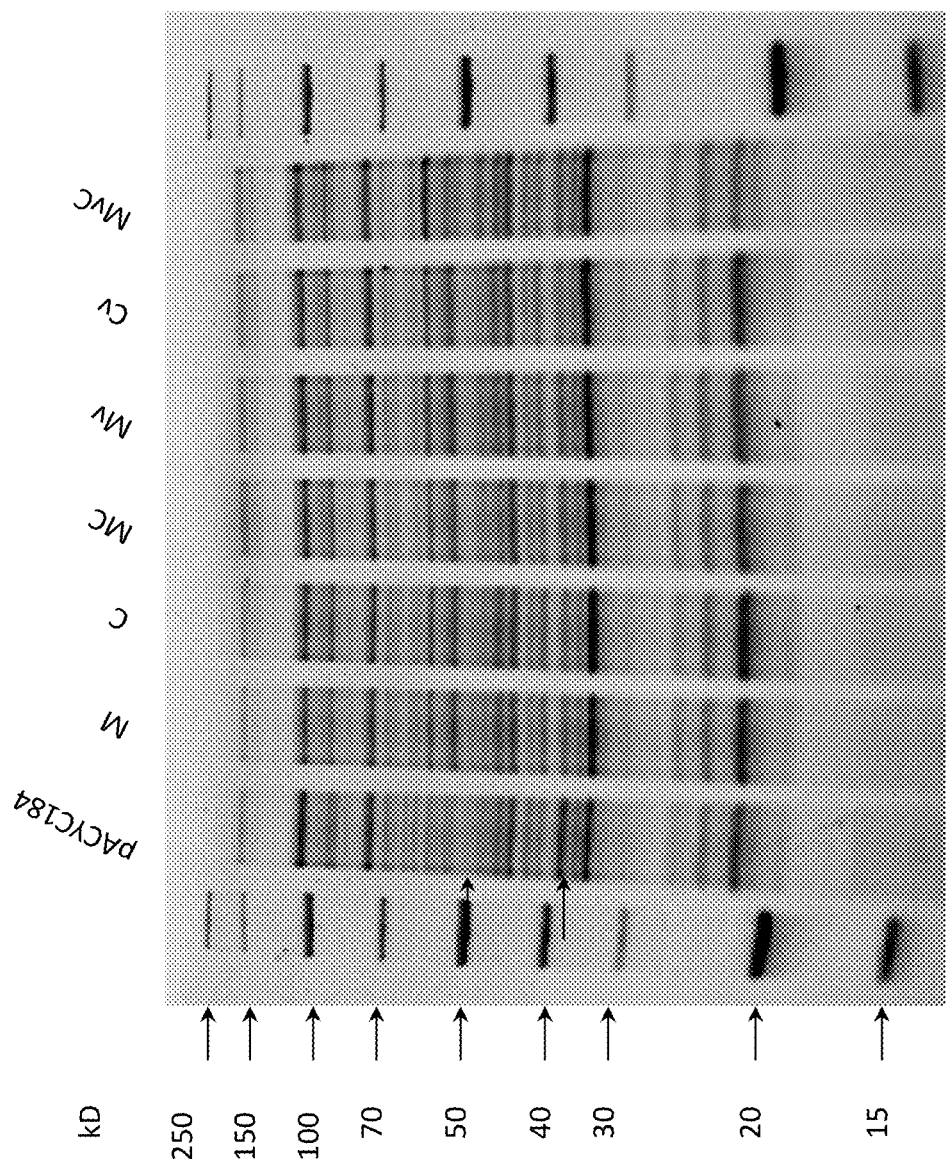
FIG. 6 Different expression levels of methylases M (Sll0729) and C (Slr0214) are not distinguishable on SDS-PAGE. Total protein in *E. coli* XL1-Blue MRF' strains harboring plasmids pACYC184, pAC-M, pAC-C, pAC-MC, pAC-Mv, pAC-Cv, pAC-MvC.
Figure 7:
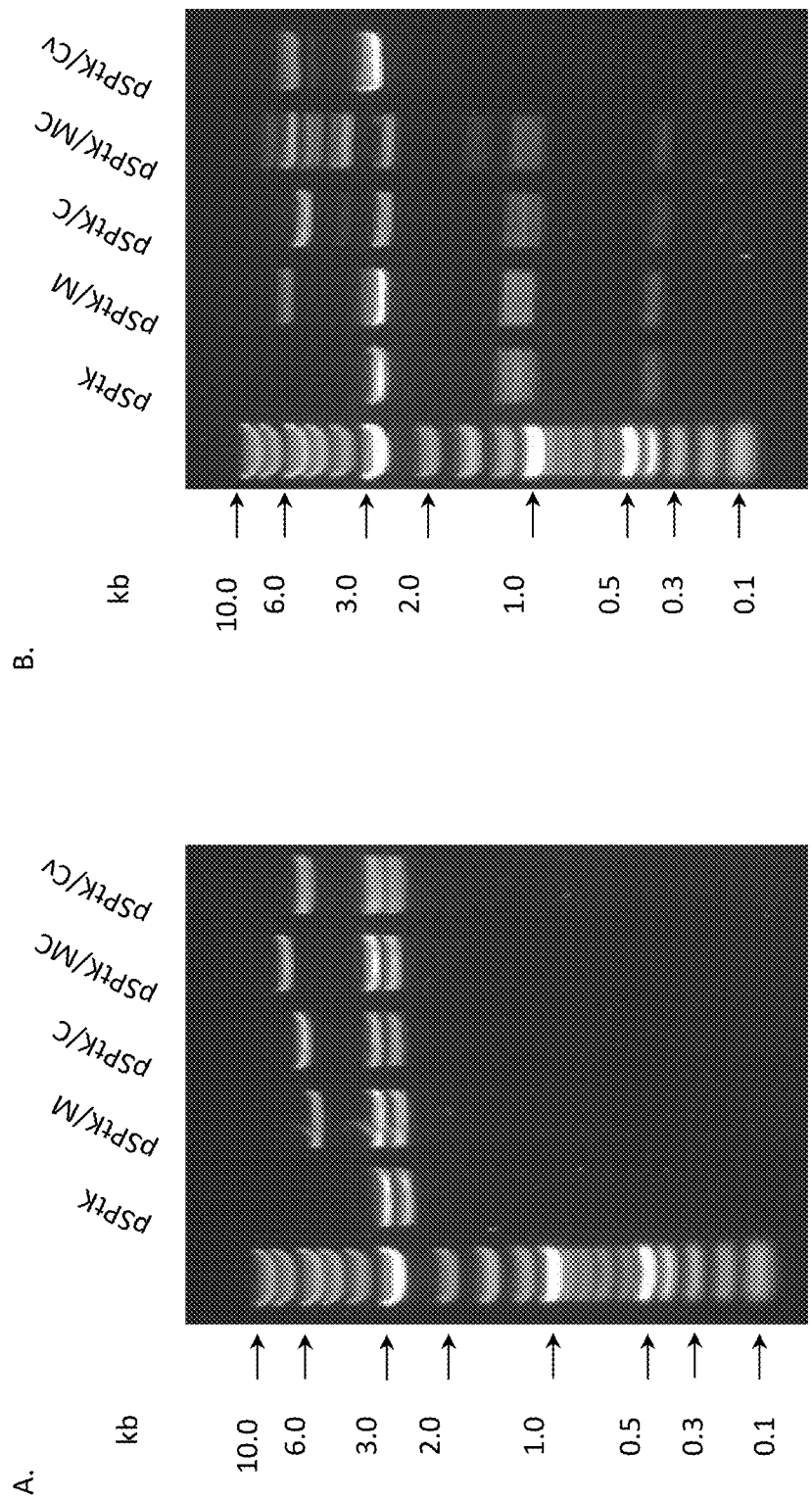
FIG. 7 The expression level of methylase C (Slr0214) got continuously increased in *E. coli* via plasmids pAC-C, pAC-MC, and pAC-Cv, respectively. Restriction digestion of plasmids to probe DNA methylation levels. (A) Plasmids digested with restriction endonucleases SacI, XbaI and XhoI. (B) Plasmids digested with PvuI. In the case of pSPtK/M, DNA is fully digestible by restriction endonuclease PvuI, while DNA of pSPtK/C is only partially digestible; DNA of pSPtK/MC is still partially digestible but to a greater extent than that of pSPtK/C; DNA of pSPtK/Cv is completely not digestible by PvuI. It indicates that the methylation level continuously increases in strains harboring pAC-C, pAC-MC, and pAC-Cv.
Figure 8:
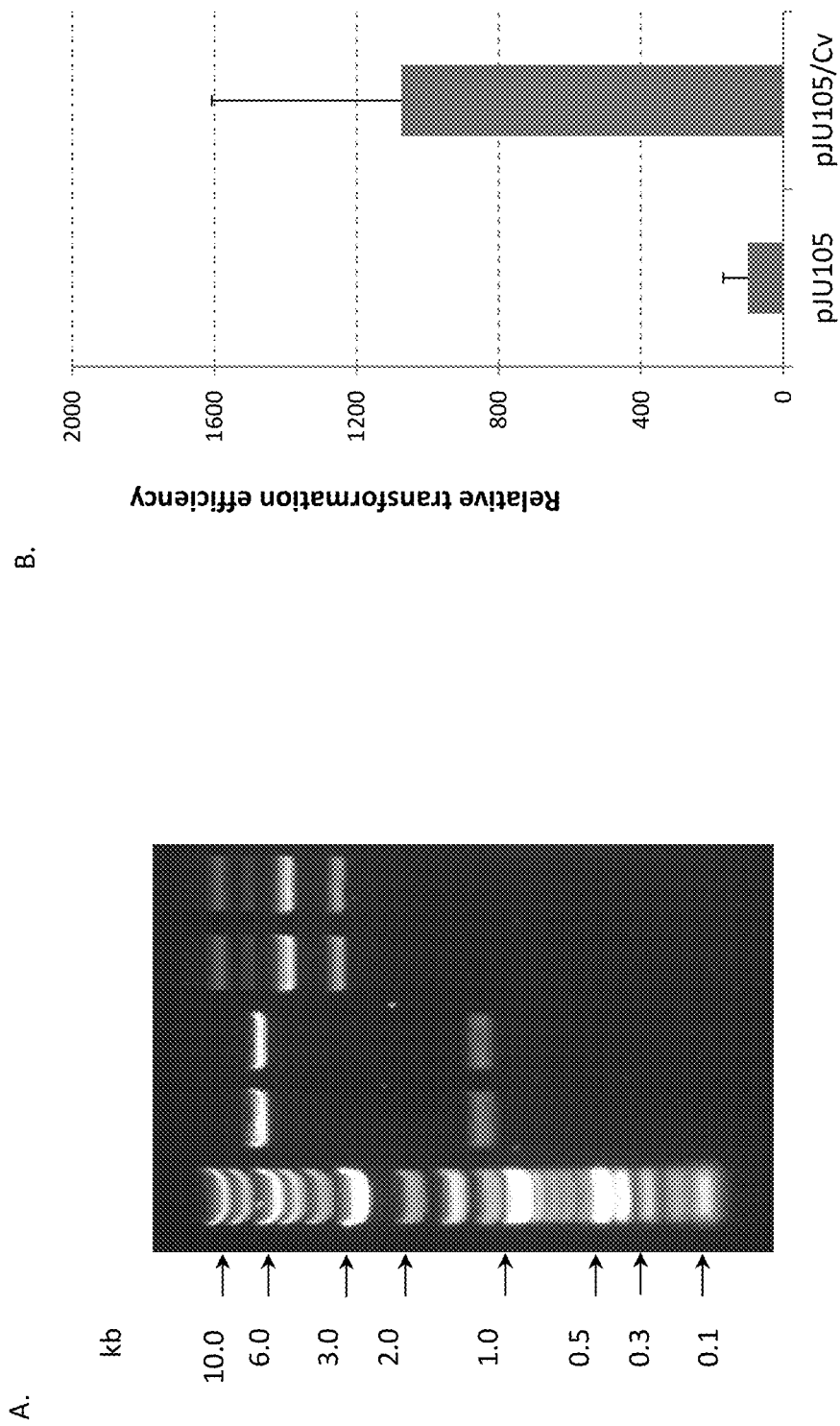
FIG. 8 Increased transformation efficiency of the integrative plasmid pJU105 into *Synechocystis* 6803. Plasmid pJU105 can be referenced from Ungerer J. et al. 2012. *Energy Environ. Sci.*, 5, 8998-9006. With help of pAC-Cv, the integrative transformation efficiency of pJU105 increased by 11-fold. Pre-methylation treatment of plasmids pSPtK and pJU105 is able to increase their integrative transformation efficiency in *Synechocystis* by one to two orders of magnitude, indicating pre-methylation of target DNA may serve as a general method to increase the transformation efficiency in *Synechocystis* 6803 and derivatives.

Our results indicate that optimization of the expression of cytosine-specific methylase C (Slr0214) played an essential role in improving the transformation efficiency, and the improvement of the transformation efficiency was proportional to the TIR of methylase C (FIG. 4, 5; Table 3). However, improved expression of cytosine-specific methylase M (Sll0729) showed little impact on the transformation efficiency in *Synechocystis* 6803 (FIG. 5), suggesting that methylase M is dispensable for the pre-methylation of foreign DNA.

It was reported that methylase C (Slr0214) specifically methylates the first cytosine of the sequence 5'-CGATCG-3' which blocks restriction digestion from the PvuI and SgfI endonucleases (which recognizes 5'-GCGATCGC-3'), while modification methylase M (Sll0729) methylates the cytosine base(s) of the sequence 5'-GGCC-3'. We screened the sequence of the integrative plasmid pSPtK and found totally two sites of 5'-CGATCG-3' and six sites of 5'-GGCC-3' along the DNA sequence of the integration fragment (FIG. 1). It is speculated that the significantly increased transformation efficiency using Help Plasmid pAC-Cv was probably due to the protection of the integration fragment from digestion by the endogenous restriction enzymes in *Synechocystis* 6803. It also suggested that restriction digestion of foreign DNA posed a significant barrier in transformation of cyanobacterium *Synechocystis* 6803.

As synthetic biology application in cyanobacteria dramatically increases in recent years, strategies to enhance the genetic transformation efficiency in cyanobacterial species have become an urgent need. In this study, two cytosine-specific methylase genes M (sll0729) and C (slr0214) were cloned from the chromosome of *Synechocystis* 6803 and expressed via Help Plasmids in the integrative-plasmid-harboring recombinant *E. coli*. Transformation results indicated that while expression of methylase gene M (sll0729) had little effect on the integrative efficiency in *Synechocystis* 6803, expression of methylase gene C (slr0214) was able to dramatically increase the transformation efficiency in *Synechocystis* 6803. Optimization of the C (slr0214) expression via redesigning the 5'-UTR to increase the translation initiation rate eventually led to approximately two orders of magnitude higher transformation efficiency in *Synechocystis* (FIG. 5).

TABLE 1

Strains and plasmids used in this research.

| | Genotype* | References |
|---|---|---|
| Strains | | |
| *E. coli* XL1-Blue MRF' | Δ(mcrA)183 Δ(mcrCB-hsdSMR-mrr)173 endA1 supE44 thi-1 recA1 gyrA96 relA1 lac [F' proAB lacI$^q$ZΔM15 Tn10 (Tet$^r$)] | Stratagene |
| *Synechocystis* sp. PCC 6803 | Wild-type | ATCC |
| Plasmids | | |
| pBS-SPtK | Amp$^R$, pUC ori, f1(+) ori, $P_{tac}$-Kan$^R$ | (36) |
| pACYC184 | Cm$^R$, Tet$^R$, p15A ori | New England BioLabs |
| pAC-M | sll0729 inserted between BamHI and SalI sites of pACYC184 | This study |
| pAC-C | slr0214 inserted between BamHI and SalI sites of pACYC184 | This study |
| pAC-MC | sll0729 and slr0214 inserted between BamHI and SalI sites of pACYC184 | This study |

TABLE 1-continued

Strains and plasmids used in this research.

| | Genotype* | References |
|---|---|---|
| pAC-Mv | pAC-M but 5'-untranslated region (UTR) optimized for sll0729 | This study |
| pAC-Cv | pAC-C but 5'-UTR optimized for slr0214 | This study |
| pAC-MCv | pAC-MC but 5'-UTR optimized for sll0729 | This study |

TABLE 2

Primers used in this invention.

Primers (5' to 3') used for DNA recobination

| Name | | Usage |
|---|---|---|
| MMS1 | GAAGATCTGAGGAATAGAACTATGGAGGAAAC (SEQ ID NO: 1) | pAC-M |
| MMS2 | ATGGTCGACTAGGATCCGTTATAACCTTCAGGATT ACTCATG (SEQ ID NO: 2) | pAC-M |
| MMS5 | GACGATATCAGGAGGAATAGAACTATGGAGGAAA C (SEQ ID NO: 3) | pAC-Mv, pAC-MCv |
| Ptet2 | GACGATATCAGCAATTTAACTGTGATAAACTAC (SEQ ID NO: 4) | pAC-Mv, pAC-MCv |
| CSM1 | TAGGATCCAGGAAAAACCATGGCCAGAC (SEQ ID NO: 5) | pAC-C |
| CSM2 | ATGGTCGACTTGGAGTGGTAATTCTAACTGC (SEQ ID NO: 6) | pAC-C |
| CSM3 | GATAAGCTTTAATGCGGTAGTTTATCACAGTTAAA TTGCTAGGAGGAAAAACCATGGCCAGAC (SEQ ID NO: 7) | pAC-Cv |
| CSM4 | CATGGATCCTAATTCTAACTGCTTTAGGAATG (SEQ ID NO: 8) | pAC-Cv |

Primers used for RT-qPCR

| Name | | Targets |
|---|---|---|
| 16S-F2 | CCACGCCTAGTATCCATCGT (SEQ ID NO: 9) | Synechocystis 16S |
| 16S-R2 | TGTAGCGGTGAAATGCGTAG (SEQ ID NO: 10) | Synechocystis 16S |
| MMS1 | TTACCGATTCTTCCATTGATAG (SEQ ID NO: 11) | sll0729 |
| MMS2 | TCCTCGGAATCATCATAGG (SEQ ID NO: 12) | sll0729 |
| CSMq1 | CCAATACACTACGCCTTACCTAG (SEQ ID NO: 13) | slr0214 |
| CSMq2 | CCGGCAAATCCTCAACAG (SEQ ID NO: 14) | slr0214 |

TABLE 3

Gibbs free energy and translation initiation rates[a]

| | $\Delta G_{total}$ for M | $\Delta G_{total}$ for C |
|---|---|---|
| pAC-M | 5.13 (249) | — |
| pAC-C | — | 6.35 (143) |
| pAC-MC | 5.13 (249) | 3.65 (484) |
| pAC-Mv | −2.02 (6214) | — |
| pAC-Cv | — | −4.79 (21556) |
| pAC-MCv | −2.02 (6214) | 3.65 (484) |

[a]Values are shown in a unit of kcal/mol; values in brackets indicate the relative translation initiation rate in each case.

All embodiments of any aspect of the invention can be combined with other embodiments of any aspect of the invention unless the context clearly dictates otherwise.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

What is claimed is:

1. A method utilizing pre-methylated DNA that has been methylated in situ and then isolated from a recombinant host cell for enhanced efficiency transformation of cyanobacteria versus transformation with DNA that has not been pre-methylated and isolated from said recombinant host cell, comprising the step of:
transforming said cyanobacteria by adding DNA comprising a plasmid mixture to a culture of said cyanobacteria under conditions and for a time sufficient to effect transformation, wherein said DNA comprising said plasmid mixture has been methylated in, and isolated from, said recombinant host cell.

2. The method of claim 1, wherein the cyanobacteria is cyanobacterium *Synechocystis* sp. PCC 6803.

3. The method of claim 1, wherein said DNA has been methylated by a cytosine-specific methyltransferase.

4. The method of claim 3, wherein said methyltransferase is encoded by gene slr0214 from *Synechocystis* 6803.

5. The method of claim 3, wherein said methyltransferase targets the first cytosine of the PvuI site (5'-CGATCG-3').

6. The method of claim 3, wherein integrative plasmid pJU105 is methylated by said cytosine-specific methyltransferase.

7. The method of claim 3, wherein integrative plasmid pBS-SPtK is methylated by said cytosine-specific methyltransferase.

8. The method of claim 1, wherein said recombinant host cell comprises *E. coli*.

9. The method of claim 1, wherein said DNA comprises integrative plasmid pJU105.

10. The method of claim 1, wherein said DNA comprises integrative plasmid pBS-SPtK.

11. A method utilizing pre-methylated DNA that has been methylated in situ and then isolated from a recombinant host cell for enhanced efficiency transformation of a cyanobacteria cell versus transformation with DNA that has not been pre-methylated and isolated from said recombinant host cell, comprising transforming said cyanobacteria cell by adding DNA comprising a plasmid mixture to a culture that contains said cyanobacteria cell under conditions and for a time sufficient to effect transformation, wherein said DNA comprising said plasmid mixture has been methylated in, and isolated from, said recombinant host cell, and wherein said DNA integrates into a genome of the cyanobacteria cell.

12. The method of claim 11, wherein the cyanobacteria is cyanobacterium *Synechocystis* sp. PCC 6803.

13. The method of claim 11, wherein said DNA has been methylated by a cytosine-specific methyltransferase.

14. The method of claim 13, wherein said methyltransferase is encoded by gene slr0214 from *Synechocystis* 6803.

15. The method of claim 13, wherein said methyltransferase targets the first cytosine of the PvuI site (5'-CGATCG-3').

16. The method of claim 13, wherein integrative plasmid pJU105 is methylated by said cytosine-specific methyltransferase.

17. The method of claim 13, wherein integrative plasmid pBS-SPtK is methylated by said cytosine-specific methyltransferase.

18. The method of claim 11, wherein said recombinant host cell comprises *E. coli*.

19. The method of claim 11, wherein said DNA comprises integrative plasmid pJU105.

20. The method of claim 11, wherein said DNA comprises integrative plasmid pBS-SPtK.

* * * * *

UNITED STATES PATENT AND TRADEMARK OFFICE
CERTIFICATE OF CORRECTION

PATENT NO. : 10,378,019 B2
APPLICATION NO. : 14/842671
DATED : August 13, 2019
INVENTOR(S) : Bo Wang et al.

Page 1 of 1

It is certified that error appears in the above-identified patent and that said Letters Patent is hereby corrected as shown below:

In the Claims

Claim 1, Line 20, "in situ" should read --*in situ*--

Claim 4, Line 36, "slr0214" should read --*slr0214*--

Claim 5, Line 38, "Pvul" should read --*Pvul*--

Claim 11, Line 19, "in situ" should read --*in situ*--

Claim 14, Line 34, "slr0214" should read --*slr0214*--

Claim 15, Line 36, "Pvul" should read --*Pvul*--

Signed and Sealed this
Twenty-ninth Day of October, 2019

Andrei Iancu
*Director of the United States Patent and Trademark Office*

SEQUENCE LISTING

<160> NUMBER OF SEQ ID NOS: 14

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
gaagatctga ggaatagaac tatggaggaa ac                           32

<210> SEQ ID NO 2
<211> LENGTH: 42
<212> TYPE: DNA
<213> ORGANISM: Artificial Sequence
<220> FEATURE:
<223> OTHER INFORMATION: primer

<400> SEQUENCE: 2
atggtcgact aggatccgtt ataaccttca ggattactca tg                42

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
gacgatatca ggaggaatag aactatggag gaaac                        35

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
gacgatatca gcaatttaac tgtgataaac tac                          33

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
taggatccag gaaaaccat ggccagac                                 28

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
atggtcgact tggagtggta attctaactg c                            31

<210> SEQ ID NO 7
<211> LENGTH: 63
<212> TYPE: DNA
<213> ORGANISM: Artificial Sequence -continued
<220> FEATURE:
<223> OTHER INFORMATION: primer

<400> SEQUENCE: 7
gataagcttt aatgcggtag tttatcacag ttaaattgct aggaggaaaa accatggcca        60
gac                                                                       63

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
catggatcct aattctaact gctttaggaa tg                                       32

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ccacgcctag tatccatcgt                                                     20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgtagcggtg aaatgcgtag                                                     20

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
ttaccgattc ttccattgat ag                                                  22

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
tcctcggaat catcatagg                                                      19

<210> SEQ ID NO 13
<211> LENGTH: 23
<212> TYPE: DNA
<213> ORGANISM: Artificial Sequence
<220> FEATURE:
<223> OTHER INFORMATION: primer

```
<400> SEQUENCE: 13
ccaatacact acgccttacc tag                                              23

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
ccggcaaatc ctcaacag                                                    18
```